United States Patent

Jahn et al.

[11] Patent Number: 5,169,426
[45] Date of Patent: Dec. 8, 1992

[54] CYCLOHEXENONE DERIVATIVES, THEIR PREPARATION AND THEIR USE FOR CONTROLLING UNDESIRABLE PLANT GROWTH

[75] Inventors: Dieter Jahn, Edingen-Neckarhaus; Rainer Becker, Bad Durkheim; Michael Keil, Freinsheim; Ulrich Schirmer, Heidelberg; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 576,197

[22] Filed: Aug. 30, 1990

Related U.S. Application Data

[63] Continuation of Ser. No. 935,297, Nov. 26, 1986, abandoned, which is a continuation-in-part of Ser. No. 764,324, Aug. 12, 1985, abandoned.

[30] Foreign Application Priority Data

Aug. 18, 1984 [DE] Fed. Rep. of Germany ....... 3430483
Jan. 25, 1985 [DE] Fed. Rep. of Germany ....... 3502391

[51] Int. Cl.$^5$ ............... A01N 43/20; C07D 303/36; C07D 331/02
[52] U.S. Cl. ........................................... 71/88; 71/90; 549/90; 549/545; 549/546
[58] Field of Search ............ 549/545, 546, 90; 71/88, 90

[56] References Cited

U.S. PATENT DOCUMENTS 3,773,824  11/1973  Strong ................. 549/484

Primary Examiner—C. Warren Ivy
Assistant Examiner—Ba K. Trinh
Attorney, Agent, or Firm—Keil & Weinkauf

[57] ABSTRACT

Cyclohexenone derivatives of the formula

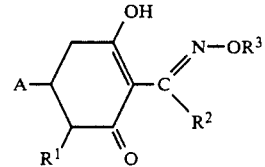

where $R^1$, $R^2$, $R^3$ and A have the meanings stated in the description, herbicides which contain these compounds as active ingredients, and a method for controlling undesirable plant growth.

9 Claims, No Drawings

CYCLOHEXENONE DERIVATIVES, THEIR PREPARATION AND THEIR USE FOR CONTROLLING UNDESIRABLE PLANT GROWTH

This application is a continuation of Ser. No. 06/935,297, filed Nov. 26, 1986, now abandoned, which is a CIP of Ser. No. 06/764,324, filed Aug. 12, 1985, now abandoned.

The present invention relates to cyclohexenone derivatives, herbicides which contain these compounds as active ingredients, and a method for controlling undesirable plant growth.

It has been disclosed that cyclohexenone derivatives can be used for controlling undesirable grasses in broad-leaved crops (DE-A-2 439 104). Moreover, DE-A-3 219 490 and DE-A-3 032 973 disclose derivatives which are cycloalkenyl-substituted in the 5-position and which likewise possess herbicidal activity.

We have found that cyclohexenone derivatives of the formula I

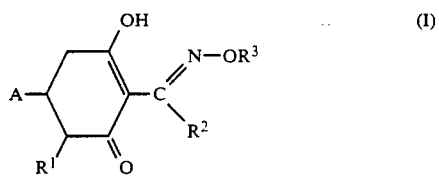

where A is cycloalkyl radical of 5 to 12 ring members or a bicyclohept-2-yl radical which is fused with an oxirane or thiirane ring, which is unsubstituted or, in the case of cyclohexyl, substituted by not more than three methyl groups, $R^1$ is hydrogen, methoxycarbonyl or cyano, preferably hydrogen, $R^2$ is alkyl of 1 to 4 carbon atoms and $R^3$ is alkyl of 1 to 3 carbon atoms, alkenyl of 3 or 4 carbon atoms, haloalkenyl of 3 or 4 carbon atoms which has 1, 2 or 3 halogen substituents, or propargyl, and salts of these compounds have a good herbicidal action, preferably against species from the grass family (Gramineae). They have a selective action in broad-leaved crops and in monocotyledon crops which do not belong to the Gramineae.

The compounds of the formula I can occur in a plurality of forms, all of which are embraced by the claims:

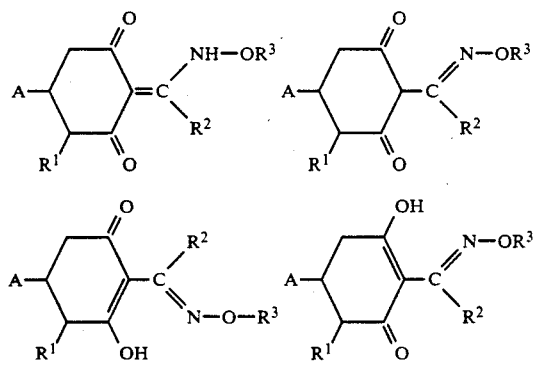

In formula I, A is a cycloalkyl radical having 5 to 12, preferably 5 to 8, ring members which is fused with an oxirane or thiirane ring which is unsubstituted or, in the case of the cyclohexyl radical, substituted by not more than three methyl groups, e.g. epoxycyclopentyl, epoxycyclohexyl, epoxycycloheptyl, epoxycyclooctyl, epoxycyclododecyl, epoxymethylcyclohexyl, dimethylepoxycyclohexyl, epoxytrimethylcyclohexyl, epoxybicycloheptyl, epithiocyclopentyl, epithiocyclohexyl or epithiobicycloheptyl. 3,4-Epoxycyclopentyl is particularly preferred.

In formula I, $R^2$ is straight-chain or branched alkyl of 1 to 4, preferably 2 or 3, carbon atoms, i.e. methyl, ethyl, n-propyl, isopropyl, n-butyl, sec.-butyl, isobutyl or tert.-butyl.

In formula I, $R^3$ is propargyl, alkyl of 1 to 3 carbon atoms, alkenyl of 3 or 4 carbon atoms or haloalkenyl of 3 or 4 carbon atoms which may contain not more than three halogen substituents, e.g. methyl, ethyl, n-propyl, isopropyl, n-butyl, sec.-butyl, isobutyl, tert.-butyl, allyl, 3-chloroprop-2-enyl, 2-chloroprop-2-enyl, 1,3-dichloroprop-2-enyl or 2,3,3-trichloroprop-2-enyl.

Suitable salts of the compounds of the formula I are those which can be used in agriculture, for example the alkali metal salts, in particular the potassium or sodium salts, alkaline earth metal salts, in particular calcium, magnesium or barium salts, manganese, copper, zinc and iron salts, and ammonium, sulfonium and phosphonium salts.

The compounds of the formula I can be obtained by reacting a tricarbonyl compound of the formula II

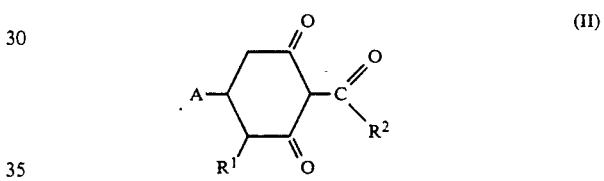

where A, $R^1$ and $R^2$ have the above meanings, with a hydroxylamine derivative $R^3O$—$NH_3Y$, where $R^3$ has the above meaning and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides or oxides of alkali metals or alkaline earth metal, in particular those of sodium, potassium, magnesium and calcium. It is also possible to use organic bases, such as pyridine or tertiary amines.

Examples of suitable diluents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and cyclic ethers, such as dioxane or tetrahydrofuran. Mixtures of these diluents may also be used.

The reaction is complete after a few hours, and the product can then be isolated by evaporating down the mixture, adding water and extracting with a non-polar solvent, such as methylene chloride, and distilling off the solvent under reduced pressure.

The compounds of the formula I may furthermore be obtained by reacting a compound of the formula II with a hydroxylamine of the formula $R^3O$—$NH_2$, where $R^3$ has the above meanings, in an inert diluent at from 0° C. to the boiling point of the reaction mixture, in particular from 15° to 70° C. If necessary, the hydroxylamine can be employed in aqueous solution.

Examples of suitable diluents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. Sodium alcoholates and potassium alcoholates may also serve as bases.

The other metal salts, for example the manganese, copper, zinc, iron, calcium, magnesium and barium salts, can be prepared from the sodium salts by reaction with the corresponding metal chlorides in aqueous solution. Ammonium, sulfonium and phosphonium salts can be obtained by reacting compounds of the formula I with ammonium, sulfonium or phosphonium hydroxides, if necessary in aqueous solution.

The tricarbonyl compounds of the formula II are novel. They can be prepared by conventional methods (Tetrahedron Lett. 29 (1975), 2491) from cyclohexane-1,3-diones of the formula III, which may also occur in the tautomeric forms IIIa and IIIb

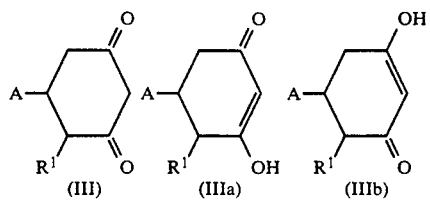

It is also possible to prepare the novel compounds of the formula II via the enol-ester intermediates which are obtained, possibly as an isomer mixture, in the reaction of compounds of the formula III, and undergo rearrangement in the presence of an imidazole or pyridine derivative (JP-A-63052/1979).

As is evident from the statements above, the tricarbonyl compounds of the formula II are useful intermediates in the preparation of herbicidal cyclohexenone derivatives of the formula I.

The compounds of the formula III can be obtained by methods which are known from the literature, as is evident from the scheme below:

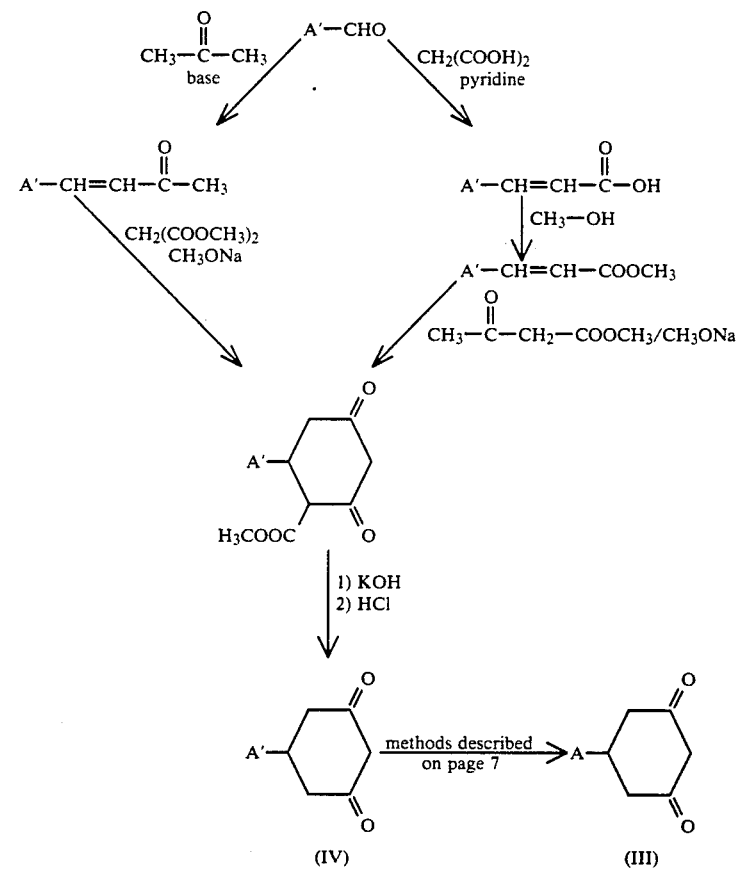

A' is a cycloalkenyl radical of 5 to 12 ring members or a bicyclo-2.2.1.-hepten-2-yl, corresponding to the substituent A Aldehydes of the general formula A'—CHO are well-known or can be obtained in a conventional manner.

The oxirane (epoxide) structure can be obtained at the end of the reaction sequence in a conventional manner by reacting the compounds of formula IV with a peroxy compound, such as hydrogen peroxide, tert.-butyl hydroperoxide, performic acid or m-chloroperbenzoic acid, or with atmospheric oxygen.

They can also be synthesized by elimination of hydrogen halide from 1,2-halohydrins generated from the corresponding olefins.

The thiirane compounds can be prepared either by reacting the corresponding epoxides with thiocyanates or thiourea, as described in, for example, J. Chem. Soc. 1946, 1050, or by reacting the corresponding unsaturated derivatives with sulfur transfer reagents, such as arylthiosulfenyl chlorides (Chemistry of Heterocyclic Compounds, vol. 42, page 340).

The Examples which follow illustrate the preparation of the cyclohexenone derivatives of the formula I. Parts by weight bear the same relation to parts by volume as that of the kilogram to the liter.

The $^1$H-NMR spectra were recorded on solutions in deuterochloroform as a solvent, using tetramethylsilane as an internal standard. The $^1$H chemical shifts are each stated in [ppm]. The following abbreviations were used to describe the signal structure: s=singlet, d=doublet, t=triplet, q=quartet and m=multiplet, strongest signal.

EXAMPLE 1

3.5 parts by weight of 2-butyryl-5-(3,4-epoxycyclohexyl)-cyclohexane-1,3-dione, 1.5 parts by weight of allyloxyammonium chloride and 1.2 parts by weight of sodium bicarbonate in 50 parts by volume of methanol were stirred for 16 hours at room temperature. The solvent was distilled off under reduced pressure, the residue was stirred with 50 parts by volume of water and 50 parts by volume of dichloromethane, the organic phase was separated off, the aqueous phase was extracted once with 50 parts by volume of dichloromethane, the combined organic phases were dried over sodium sulfate and the solvent was distilled off under reduced pressure. 2-(1-Allyloxyiminobutyl)-5-(3,4-epoxycyclohexyl)-3-hydroxycyclohex-2-en-1-one (active ingredient No. 1) was obtained.

$^1$H-NMR spectrum: 0.95 (t), 2.9 (q), 5.3 (m).

EXAMPLE 2

3.5 parts by weight of 2-butyryl-5-(3,4-epoxycyclohexyl)-cyclohexane-1,3-dione and 0.8 part by weight of ethoxyamine in 100 parts by volume of methanol were stirred for 16 hours at room temperature. The solvent was distilled off under reduced pressure, the residue was dissolved in dichloromethane, the solution was washed with 5% strength by weight hydrochloric acid and water and dried over sodium sulfate, and the solvent was distilled off under reduced pressure. 2-(1-Ethoxyiminobutyl)-5-(3,4-epoxycyclohexyl)-3-hydroxycyclohex-2-en-1-one (active ingredient No. 2) was obtained.

$^1$H-NMR spectrum: 1.3 (t), 3.2 (m), 4.1 (d).

EXAMPLE 3

9 parts by weight of 2-(1-propoxyiminobutyl)-5-(cyclohex-3-enyl)-3-hydroxycyclohex-2-en-1-one were dissolved in 100 parts by weight of dichloromethane, and 5.8 parts by weight of m-chloroperbenzoic acid (about 80%) in 100 parts by volume of dichloromethane were added dropwise at 5°–10° C. After one hour, the course of the reaction was checked by means of thin layer chromatography using a precoated silica gel 60 TLC plate and 1:1 cyclohexane/ethyl acetate as the mobile phase. Further m-chloroperbenzoic acid was added dropwise until conversion was complete. Excess peracid was destroyed by shaking with sodium thiosulfate solution. Thereafter, the mixture was extracted twice with semi-saturated sodium bicarbonate solution and once with water, the organic phase was dried over sodium sulfate and the solvent was distilled off under reduced pressure. 2-(1-Propoxyiminobut-2-yl)-5-(3,4-epoxycyclohexyl)-3-hydroxycyclohex-2-en-1-one (active ingredient No. 3) was obtained.

$^1$H-NMR spectrum: 2.2 (m), 3.1 (m), 4.0 (q).

The compounds below were obtained by methods similar to those described in the Examples.

| Active ingredient no. | A | $R^1$ | $R^2$ | $R^3$ | $^1$H-NMR data |
| --- | --- | --- | --- | --- | --- |
| 4 | 3,4-epoxy-1-methyl-cyclohexyl | H | n-propyl | ethyl | 0.85 (s),1.3 (t),2.9 (m) |
| 5 | 3,4-epoxy-1-methyl-cyclohexyl | H | n-propyl | allyl | |
| 6 | 3,4-epoxy-4-methyl-cyclohexyl | H | n-propyl | ethyl | 1.0 (t),1.3 (s),2.5 (m) |
| 7 | 3,4-epoxy-4-methyl-cyclohexyl | H | n-propyl | allyl | |
| 8 | 3,4-epoxy-6-methyl-cyclohexyl | H | n-propyl | ethyl | 0.95 (t),1.6 (m),4.1 (q) |
| 9 | 3,4-epoxy-6-methyl-cyclohexyl | H | n-propyl | allyl | 0.9 (m),2.9 (d),4.55 (d) |
| 10 | 3,4-epoxy-6-methyl-cyclohexyl | H | n-propyl | 3-chloroallyl (trans) | |
| 11 | 1,2-epoxy-2,6,6,-trimethyl-cyclohexyl | H | n-propyl | ethyl | 1.40 (s),2.9 (m),4.1 (q) |
| 12 | 1,2-epoxy-2,6,6-trimethyl-cyclohexyl | H | n-propyl | ethyl | |
| 13 | 3,4-dimethyl-3,4-epoxy-cyclohexyl | H | n-propyl | ethyl | 0.95 (t),1.35 (m),4.10 (q) |
| 14 | 3,4-dimethyl-3,4-epoxy-cyclohexyl | H | n-propyl | allyl | |
| 15 | 1,2-epoxy-cyclooctyl | H | n-propyl | ethyl | 1.0 (t),1.30 (t),4.1 (q) |
| 16 | 1,2-epoxy-cyclooctyl | H | n-propyl | allyl | 0.95 (t),1.35 (s),2.95 (m) |
| 17 | 4,5-8,9-diepoxy-cyclododecyl | H | n-propyl | ethyl | |
| 18 | 4,5-8,9-diepoxy-cyclododecyl | H | n-propyl | allyl | |
| 19 | 3,4-epoxy-cyclopentyl | H | n-propyl | ethyl | |
| 20 | 3,4-epoxy-cyclopentyl | H | n-propyl | allyl | |
| 21 | 3,4-epoxy-cyclopentyl | H | n-propyl | 3-chlorallyl (trans) | |
| 22 | 3,4-epoxy-cyclopentyl | H | n-propyl | propargyl | |
| 23 | 3,4-epoxy-cyclopentyl | H | ethyl | ethyl | 1.14 (t),2.9 (q),3.5 (s),4.11 (q) |
| 24 | 5,6-epoxy-bicyclo [2.2.1]-hept-2-yl | H | ethyl | propargyl | |
| 25 | 5,6-epoxy-bicyclo [2.2.1]-hept-2-yl | H | ethyl | allyl | 2.5 (m),2.9 (m),4.55 (d) |
| 26 | 5,6-epoxy-bicyclo [2.2.1]- | H | ethyl | ethyl | 0.8 (d)2.5 (m),2.9 (m) |

-continued

| Active ingredient no. | A | R¹ | R² | R³ | ¹H-NMR data |
|---|---|---|---|---|---|
| | hept-2-yl | | | | |
| 27 | 5,6-epoxy-bicyclo [2.2.1]-hept-2-yl | H | n-propyl | 3-chloroallyl (trans) | 3.15 (d),4.5 (d),6.3 (m) |
| 28 | 5,6-epoxy-bicyclo [2.2.1]-hept-2-yl | H | n-propyl | ethyl | 1.3 (t),2.9 (s),4.1 (q) |
| 29 | 5,6-epoxy-bicyclo [2.2.1]-hept-2-yl | H | n-propyl | allyl | 1.0 (t),2.5 (m),4.5 (d) |
| 30 | 5,6-epoxy-bicyclo [2.2.1]-hept-2-yl | H | n-propyl | propargyl | = 1.0 (t),2.6 (m),4.65 (s) |
| 31 | 2,3-epoxy-cyclohexyl | H | n-propyl | ethyl | |
| 32 | 2,3-epoxy-cyclohexyl | H | n-propyl | allyl | |
| 33 | 3,4-epithio-cyclohexyl | H | n-propyl | ethyl | 0.95 (t),2.90 (d),3.15 (m) |
| 34 | 3,4-epithio-cyclohexyl | H | n-propyl | allyl | |
| 35 | 5,6-epithio-bicyclo-[2.2.1]hept-2-yl | H | n-propyl | ethyl | |
| 36 | 5,6-epithio-bicyclo-[2.2.1]hept-2-yl | H | n-propyl | allyl | |
| 37 | 3,4-epithio-cyclopentyl | H | n-propyl | ethyl | |
| 38 | 3,4-epithio-cyclopentyl | H | n-propyl | allyl | |
| 39 | 3,4-epithio-cyclopentyl | H | ethyl | allyl | |
| 40 | 3,4-epithio-cyclopentyl | H | ethyl | ethyl | |
| 41 | 2,3-epithio-cyclopentyl | H | ethyl | ethyl | |
| 42 | 2,3-epithio-cyclopentyl | H | ethyl | allyl | |
| 43 | 2,3-epithio-cyclopentyl | H | n-propyl | allyl | |
| 44 | 2,3-epithio-cyclopentyl | H | n-propyl | ethyl | |
| 45 | 2,3-epithio-cyclopentyl | H | n-propyl | 3-chloroallyl (trans) | |
| 46 | 2,3-epithio-cyclohexyl | H | n-propyl | ethyl | |
| 47 | 2,3-epithio-cyclohexyl | H | n-propyl | allyl | |
| 48 | 2,3-epithio-cyclohexyl | H | ethyl | ethyl | |
| 49 | 2,3-epithio-cyclohexyl | H | ethyl | allyl | |
| 50 | 4,5-epoxy-cyclooctyl | H | n-propyl | ethyl | 1.0 (t),1.35 (t),4.1 (q) |
| 51 | 4,5-epoxy-cyclooctyl | H | n-propyl | allyl | 1.0 (t),2.9 (m),4.55 (d) |
| 52 | 4,5-epoxy-cyclooctyl | H | ethyl | ethyl | 1.35 (t),2.9 (m),4.1 (q) |
| 53 | 4,5-epoxy-cyclooctyl | H | ethyl | allyl | 1.15 (t),2.9 (m),4.5 (d) |
| 54 | 4,5-epoxy-cyclooctyl | H | ethyl | 3-chloroallyl (trans) | 1.15 (t),2.9 (m),4.55 (d) |
| 55 | 4,5-epoxy-cyclooctyl | H | n-propyl | 3-chloroallyl (trans) | 0.95 (t),1.5 (m),4.55 (d) |
| 56 | 4,5-8,9-diepoxy-cyclododecyl | H | ethyl | ethyl | 1.2 (t),1.3 (m),4.1 (q) |
| 57 | 3,4-epoxy-6-methyl-cyclohexyl | H | ethyl | ethyl | 1.35 (t),2.9 (q).4.1 (q) |
| 58 | 3,4-epoxy-6-methyl-cyclohexyl | H | ethyl | allyl | 1.15 (t),2.9 (m),4.5 (d) |
| 59 | 2,6-dimethyl-3,4-epoxycyclohexyl | H | n-propyl | ethyl | 1.3 (t),2.9 (s),4.1 (q) |
| 60 | 2,6-dimethyl-3,4-epoxycyclohexyl | H | n-propyl | 3-chloroallyl (trans) | 1.15 (t),28 (m),6.35 (m) |
| 61 | 5,6-epoxy-bicyclo[2.2.1]-hept-2-yl | H | ethyl | 3-chloroallyl (trans) | 1.15 (t),2.5 (m),4.55 (d) |
| 62 | 3,4-epoxy-cyclohexyl | H | ethyl | ethyl | 1.3 (t),3.15 (m),4.1 (q) |
| 63 | 3,4-epoxy-cyclohexyl | H | ethyl | allyl | 1.15 (t),2.85 (d),4.55 (d) |
| 64 | 3,4-epoxy-cyclohexyl | H | ethyl | 3-chloroallyl (trans) | 1.1 (t),2.85 (d),6.3 (d) |
| 65 | 3,4-epoxy-2-methylcyclohexyl | H | n-propyl | ethyl | 1.6 (q),3.2 (s),4.1 (q) |
| 66 | 3,4-epoxy-2-methylcyclohexyl | H | n-propyl | allyl | 0.95 (t),1.85 (m),3.20 (s) |
| 67 | 3,4-epoxy-2-methylcyclohexyl | H | ethyl | ethyl | 1.3 (t),2.35 (m),4.1 (q) |
| 68 | 3,4-epoxy-2-methylcyclohexyl | H | ethyl | allyl | 2.4 (m),4.6 (d),6.0 (m) |
| 69 | 3,4-epoxy-2-methylcyclohexyl | H | ethyl | 3-chloroallyl (trans) | 1.15 (t),2.9 (q),4.55 (d) |
| 70 | 3,4-epoxy-cyclopentyl | H | ethyl | allyl | 1.13 (t),3.5 (s),4:53 (d),5.36 (m),5.97 (m) |
| 71 | 3,4-epoxy-cyclopentyl | H | ethyl | 3-chloroallyl (trans) | 1.14 (t),3.5 (s),4.55 (d),6.1 (m),6.35 (d) |
| 72 | 4,5-epoxy-cycloheptyl | H | ethyl | ethyl | |
| 73 | 4,5-epoxy-cycloheptyl | H | ethyl | allyl | |
| 74 | 4,5-epoxy-cycloheptyl | H | ethyl | 3-chloroallyl (trans) | |
| 75 | 4,5-epoxy-cycloheptyl | H | n-propyl | 3-chloroallyl (trans) | |
| 76 | 4,5-epoxy-cycloheptyl | H | n-propyl | ethyl | |
| 77 | 4,5-epoxy-cycloheptyl | H | n-propyl | allyl | |

The cyclohexanone derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 6 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 13 is intimately mixed with 97 parts by weight of particulate kaolin. A dust is obtained containing 3% by weight of the active ingredient.

VII. 30 parts by weight of compound no. 11 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.025 to 3 kg/ha, but is preferably from 0.05 to 0.5 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.06 to 0.125 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Alopecurus myosuroides, Avena fatua, Avena sativa, Digitaria sanguinalis, Echinochloa crus-galli, Glycine max., Lolium multiflorum, Setaria italica, Sinapis alba, Sorghum halepense, Sorghum bicolor, and Zea mays.

The compounds used for comparison purposes were 2-(1-allyloxyamino-n-butyl)-5-(cylcohex-1-en-4-yl)-3-hydroxycyclohex-2-en-1-one (A) and 2-(1-ethoximino-n-butyl)-5-(cyclohex-1-en-4-yl)-3-hydroxycyclohex-2-en-1-one (B) disclosed in German DE-A-3 032 973, and 2-(1-ethoxyamino-n-butyl)-5-(cyclooct-1-en-5-yl)-3-hydroxycyclohex-2-en-1-one (C) disclosed in German DE-A-3 219 490, and herbicidal agents containing these compounds.

On preemergence application, compounds nos. 4, 6, 11 and 13, for instance, had a herbicidal action on plants from the grasses family, whereas Sinapis alba, as a dicotyledonous representative, remained completely undamaged.

For example compounds nos. 4 and 6, applied postemergence at a rate of 0.125 kg/ha, had a strong herbicidal action on a broad spectrum of grassy weeds; soybeans, as dicotyledonous crop plants, suffered no damage whatsoever.

Unwanted grass species were combatted well by, for example, compounds nos. 26, 28, 52, 53, 55 and 61, whereas the broadleaved crop plant alfalfa remained completely undamaged.

Compound no. 8, for example, was suitable at low application rates for controlling undesirable grass species, and was tolerated by wheat.

Compounds nos. 1 and 2 selected by way of example control problem grasses much better than prior art comparative agents A and B, and are fully tolerated by soybeans.

Compared with prior art agent C, the degree of herbicidal action of, for instance, compound no. 50 is significantly higher, without compatibility for alfalfa being influenced.

In view of the spectrum of weeds which can be combatted, the tolerance of the active ingredients according to the invention by crop plants, the desired influence on the growth of crop plants, and in view of the numerous application methods possible, the compounds according to may be used in a large number of crop plants.

The following may be mentioned by way of example:

| Botanical name | Common name |
| --- | --- |
| Allium cepa | onions |
| Ananas comosus | pineapples |
| Arachis hypogaea | peanuts (groundnuts) |
| Aaparagus officinalis | asparagus |
| Avena sativa | oats |
| Beta Vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |

| Botanical name | Common name |
| --- | --- |
| Pinus spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. vulgare) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinnensis* (V. unguiculata) | cow peas |
| *Vitis vinifera* | grapes |
| *Zea mays* | Indian corn, sweet corn, maize (post-directed) |

To increase the spectrum of action and to achieve synergistic effects, the novel substituted cyclohexenone derivatives may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the cyclohexenone derivatives of the formula I, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

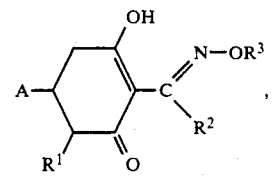

where A is an unsubstituted monocyclic cycloalkyl radical of 5 to 12 ring members or a cyclohexyl radical substituted by one to three methyl groups, wherein both said cycloalkyl and cyclohexyl radicals have two adjacent ring carbon atoms bridged by an oxygen or sulfur atom to form a fused oxirane or thiirane ring, or A is a 5,6-epoxybicylo[2.2.1]hept-2-yl radical, $R^1$ is hydrogen, methoxycarbonyl or cyano, $R^2$ is alkyl of 1 to 4 carbon atoms and $R^3$ is alkyl of 1 to 3 carbon atoms, alkenyl of 3 or 4 carbon atoms, haloalkenyl of 3 or 4 carbon atoms which has 1, 2 or 3 halogen substituents, or propargyl, or a salt thereof.

2. A cyclohexenone derivative of the formula I as set forth in claim 1, wherein $R^1$ is hydrogen.

3. A cyclohexenone derivative of the formula I as set forth in claim 1, where A is an unsubstituted monocyclic cycloalkyl radical of from 5 to 8 ring members or a cyclohexyl radical substituted by one to three methyl groups, wherein both said cycloalkyl and cyclohexyl radicals have two adjacent ring carbon atoms bridged by an oxygen or sulfur atom to form a fused oxirane or thiirane ring, or A is a 5,6-epoxybicyclo-hept-2-yl radical.

4. A cyclohexenone derivative of the formula I as set forth in claim 1, where A is 3,4-epoxycyclopentyl.

5. A cyclohexenone derivative of the formula I as set forth in claim 1, where $R^2$ is alkyl of 2 or 3 carbon atoms.

6. A herbicidal composition containing inert additives and a herbicidally effective amount of a cyclohexenone derivative of the formula I as set forth in claim 1.

7. A herbicidal composition as set forth in claim 6, containing from 0.1 to 95 wt % of a cyclohexenone derivative of the formula I.

8. A herbicidal composition as set forth in claim 6, where $R^1$ in the cyclohexenone derivative of the formula I is hydrogen.

9. A process for combatting the growth of unwanted plants, wherein the unwanted plants or the areas to be kept free from unwanted plant growth are treated with a herbicidally effective amount of a cyclohexenone derivative of the formula I as set forth in claim 1.

* * * * *

UNITED STATES PATENT AND TRADEMARK OFFICE
CERTIFICATE OF CORRECTION

PATENT NO. : 5,169,426

DATED : December 8, 1992

INVENTOR(S) : JAHN et al.

It is certified that error appears in the above-identified patent and that said Letters Patent is hereby corrected as shown below:

Claim 3, column 14, line 31: after "epoxybicyclo-" insert -- [2.2.1]- --

Signed and Sealed this

Twenty-sixth Day of October, 1993

Attest:

BRUCE LEHMAN

*Attesting Officer*  *Commissioner of Patents and Trademarks*